United States Patent [19]

Fauran et al.

[11] 4,007,187
[45] Feb. 8, 1977

[54] FURO (2,3d) PYRIMIDINES

[75] Inventors: Claude P. Fauran, Paris; Guy R. Bourgery, Colombes; Guy M. Raynaud; Nicole A. M. Dorme, both of Paris, all of France

[73] Assignee: Delalande S.A., Courbevoie, France

[22] Filed: Sept. 17, 1974

[21] Appl. No.: 506,826

[30] Foreign Application Priority Data

Oct. 2, 1973  France ............................. 73.35190
May 20, 1974  France ............................. 74.17484

[52] U.S. Cl. ..................... 260/256.4 F; 260/239 B; 260/247.2 R; 424/251
[51] Int. Cl.² ..................... C07D 239/00
[58] Field of Search ................. 260/247.2, 256.4 F

[56] References Cited
UNITED STATES PATENTS 3,037,980   6/1962   Hitchings ..................... 260/256.4 F

FOREIGN PATENTS OR APPLICATIONS 705,417   3/1965   Canada ..................... 260/256.4 F
915,303   1/1963   United Kingdom ......... 260/256.4 F

*Primary Examiner*—Paul J. Killos
*Attorney, Agent, or Firm*—Woodhams, Blanchard and Flynn

[57] ABSTRACT

Compounds of the formula

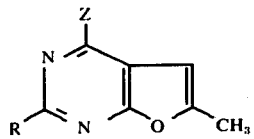

wherein R is alkyl of 1–4 carbon atoms, phenyl, or phenyl substituted by one or more halogen or trifluoromethyl, and Z is

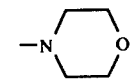

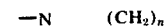

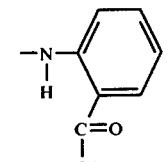

or

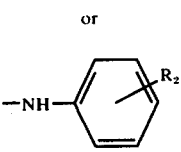

wherein $R_1$ is hydrogen, alkyl of 1–4C, 2,2-dimethyldioxolan-4-yl methyl, or 2,3-dihydroxy prop-1-yl, $R_2$ is

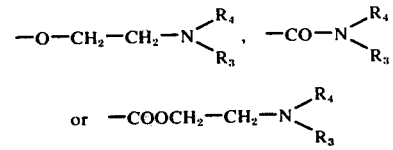

wherein

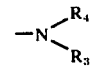

is morpholino, pyrrolidino, piperidino or hexamethyleneimino, and n is an integer from 4 to 7. The compounds are prepared by reacting R-substituted 4-chloro-2-methyl furo.(2,3d) pyrimidine with HZ. The compounds possess antiulcerous, antibronchoconstrictive and anticholinergic, analgesic, antihistamine, diuretic, cardiovascular analeptic, antiinflammatory and hypertensive properties.

4 Claims, No Drawings

FURO (2,3d) PYRIMIDINES

The present invention relates to novel furo (2,3d) pyrimidines, their process of preparation and their therapeutic application.

The compounds according to the invention correspond to the general formula:

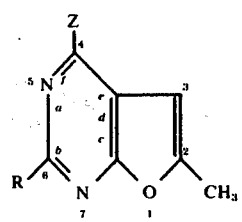
(I)

in which:
-R represents an alkyl radical containing up to 4 carbon atoms or a phenyl ring optionally substituted by one or more halogen atoms, or by a trifluoromethyl radical; and
-Z represents one of the following:

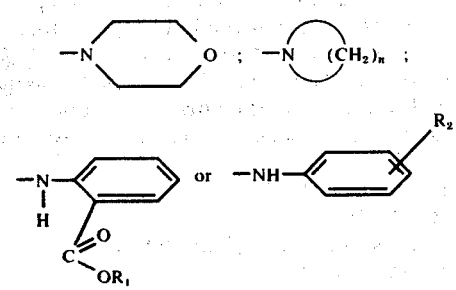

in which:
$R_1$ represents a hydrogen atom, an alkyl radical containing up to 4 carbon atoms, a 2,2-dimethyl dioxolan-4-yl methyl radical or a 2,3-dihydroxy prop-1-yl radical,
$R_2$ represents:
- a β-amino ethoxy group of formula

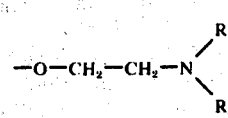

- a carboxamide group of formula

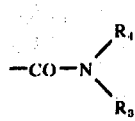

or a group of formula

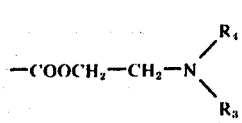

the symbol

representing a morpholino, pyrrolidino, piperidino or a hexamethyleneimino radical, and
n is an integer of between 4 and 7.

The process according to the invention consists in condensing a 4-chloro-2-methyl furo (2,3d) pyrimidine of formula:

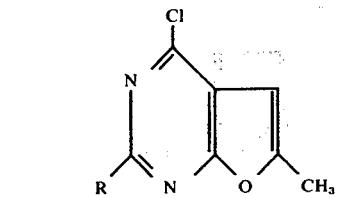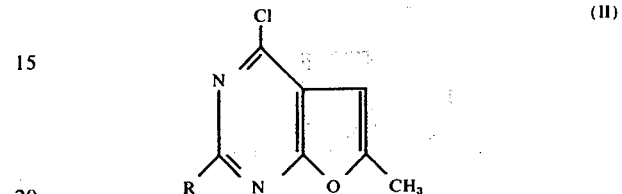
(II)

in which R represents an alkyl radical containing up to 4 carbon atoms or a phenyl ring optionally substituted by one or more halogen atoms, or by a trifluoromethyl radical, with an amine derivative of formula III

HZ'  (III)

in which Z' represents one of the following:

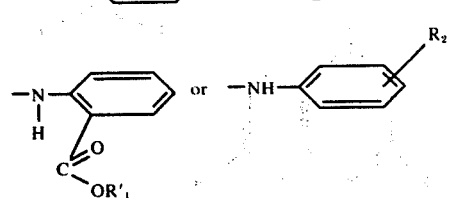
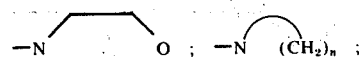

in which:
$R_1'$ represents a hydrogen atom, an alkyl radical containing up to 4 carbon atoms,
$R_2$ represents
- a β-amino ethoxy group of formula

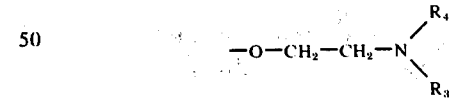

- a carboxamide group of formula

- or a group of formula

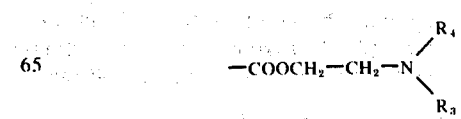

the symbol

respresenting a merpholino, pyrrolidino, piperidino or a hexamethyleneimino radical, and n is an integer of between 4 and 7. to produce a derivative corresponding to the formula:

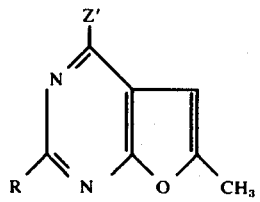

and, optionally subjecting a derivative of the formula I' in which Z' represents a 2-methoxycarbonyl anilino radical, to a transesterification in the presence of sodium with 2,2-dimethyl-4-hydroxymethyl-1,3-dioxolane, to give the derivate of formula:

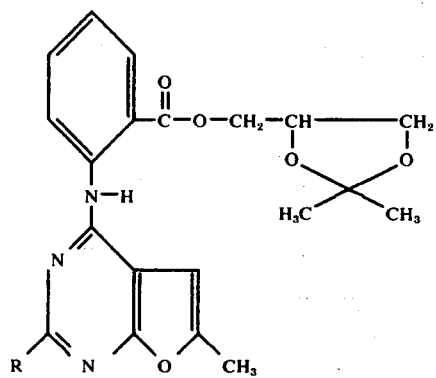

which may be then transformed into a derivative of formula:

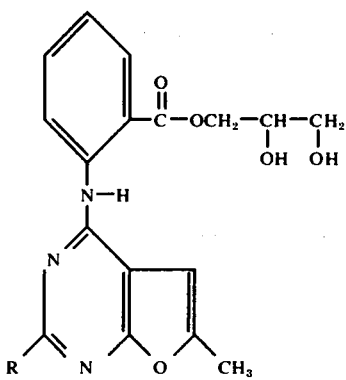

by opening of the dioxolane cycle with hydrochloric acid.

It is to be noted that the condensation of the 4-chloro-2-methyl furo (2,3d) pyrimidines of formula (II) with the amine derivatives of formula (III) is conducted:

in benzene under reflux when Z' represents a

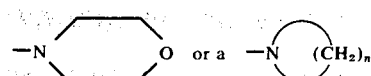

radical, in which n is an integer of between 4 and 7, and in acetic acid, in the presence of catalytic quantities of concentrated hydrochloric acid, when Z' represents a radical

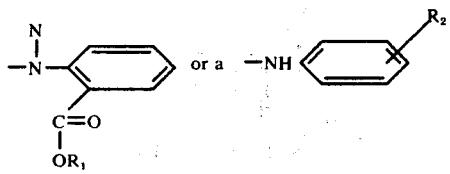

The following preparations are given, by way of example, to illustrate the invention.

EXAMPLE 1:

2-methyl-4-pyrrolidino-6-(metatrifluoromethyl phenyl) furo (2,3d) pyrimidine. (Code No. 72497)

14.2g (0.2 mol) of pyrrolidine was added, drop by drop, to a solution of 31.3g (0.1 mol) of 2-methyl-4-chloro-6-(metatrifluoromethyl phenyl) furo (2,3d) pyrimidine in 350 c.c. of benzene heated at 60° C, and the mixture was then refluxed for 6 hours. The mixture is filtered whilst warm, the filtrate is evaporated under vacuum, and the residue is recrystallised from methylethyl ketone.

Melting point = 203° C
Yield = 58%
Empirical formula = $C_{18}H_{16}F_3N_3O$
Elementary analysis:

|  | C | H | N |
|---|---|---|---|
| Calculated (%) | 62.24 | 4.64 | 12.10 |
| Found (%) | 62.13 | 4.69 | 12.03 |

EXAMPLE 2:

N-(2,6-dimethyl furo(2,3d) pyrimidin-4-yl) methyl anthranilate (Code No. 7280)

A suspension of 4.55 g. (0.03 mol) of methyl anthranilate, 5.45 g. (0.03 mol) of 2,6-dimethyl-4-chloro furo (2,3d) pyrimidine and 0.1 c.c. of concentrated hydrochloric acid in 30 c.c. of acetic acid were heated at 80° to 90° C for 30 minutes. The precipitate formed is filtered, placed in suspension with 50 c.c. of ethanol, alkalinised with concentrated ammonia, diluted with 200 c.c. of water, filtered, washed with water, recrystallised from ethanol and then from acetone.

Melting point = 186° C
Yield = 34%
Empirical formula = $C_{16}H_{15}N_3O_3$
Elementary analysis:

|  | C | H | N |
|---|---|---|---|
| Calculated (%) | 64.63 | 5.09 | 14.14 |
| Found (%) | 64.75 | 5.26 | 14.14 |

EXAMPLE 3:

N-(2,6-dimethyl furo(2,3d)pyrimidin-4-yl)-4'-methyl-2',2'-dimethyl-1',3'-dioxolane anthranilate. (Code No. 730 367)

0.3 g of sodium is dissolved, with warming, in 260 c.c. of 2,2-dimethyl-4-hydroxymethyl-1,3-dioxolane. After cooling, 65.5 g (0.22 mol) of N-(2,6-dimethyl furo(2,3d) pyrimidin-4-yl) methyl anthranilate of code No. 7280 obtained as indicated in the preceding example, is added thereto and the resultant mixture is heated for 5 hours at 140°–150° C, the methanol formed being distilled off under nitrogen. The mixture is diluted with 2l of water, filtered, washed with water and recrystallized from ethanol.

Melting point = 160° C
Yield = 50%
Empirical formula = $C_{21}H_{23}N_3O_5$
Elementary analysis:

|  | C | H | N |
|---|---|---|---|
| Calculated (%) | 63.46 | 5.93 | 10.57 |
| Found (%) | 63.42 | 5.95 | 10.37 |

EXAMPLE 4:

4-($\beta,\gamma$-2'-dihydroxypropoxycarbonyl-phen-1'yl amino)-2,6-dimethyl furo (2,3d) pyrimidine. (Code No. 730 387).

A suspension of 58g (0.147 mol) of N-(2,6-dimethyl furo (2,3d) pyrimidin-4-yl)-4'-methyl-2',2'-dimethyl-1',3'-dioxolane anthranilate of Code No. 730 367 obtained as indicated in example 3, in 500 c.c. of 2N hydrochloric acid is heated for 45 minutes under reflux. The mixture is filtered whilst warm, neutralized with 100 c.c. of triethylamine, the precipitate formed is filtered, washed with water and recrystallised from ethanol.

Melting point = 179° C
Yield = 30%
Empirical formula = $C_{18}H_{19}N_3O_5$
Elementary analysis:

|  | C | H | N |
|---|---|---|---|
| Calculated (%) | 60.49 | 5.36 | 11.70 |
| Found (%) | 60.62 | 5.36 | 11.71 |

The compounds listed in the following Table I have been prepared according to the same mode of operation.

TABLE I

| Code No. | R | −Z | Empirical Formula | Molecular Wt. | Melting Point (° C) | Yield % |  | C | H | N |
|---|---|---|---|---|---|---|---|---|---|---|
| 72 498 | $F_3C$-phenyl- | -N(cyclohexyl) | $C_{19}H_{18}F_3N_3O$ | 361.36 | 129 | 29 | Calculated (%) | 63.15 | 5.02 | 11.63 |
|  |  |  |  |  |  |  | Found (%) | 63.00 | 5.06 | 11.55 |
| 72 557 | " | -N(morpholinyl) | $C_{18}H_{16}F_3N_3O_2$ | 363.33 | 178 | 42 | Calculated (%) | 59.50 | 4.44 | 11.57 |
|  |  |  |  |  |  |  | Found (%) | 59.36 | 4.49 | 11.67 |
| 72 535 | " | -N(cycloheptyl) | $C_{20}H_{20}F_3N_3O$ | 375.38 | 126 | 53 | Calculated (%) | 63.99 | 5.37 | 11.19 |
|  |  |  |  |  |  |  | Found (%) | 63.77 | 5.45 | 11.02 |
| 72 561 | " | -N(cyclooctyl) | $C_{21}H_{22}F_3N_3O$ | 389.41 | 145 | 45 | Calculated (%) | 64.77 | 5.69 | 10.79 |
|  |  |  |  |  |  |  | Found (%) | 64.74 | 5.77 | 10.85 |
| 71 384 | Cl-phenyl- | -N(pyrrolidinyl) | $C_{17}H_{16}ClN_3O$ | 313.78 | 186 | 43 | Calculated (%) | 65.07 | 5.14 | 13.39 |
|  |  |  |  |  |  |  | Found (%) | 64.89 | 5.15 | 13.22 |
| 72 544 | Cl-phenyl- | -N(piperidinyl) | $C_{18}H_{18}ClN_3O$ | 327.81 | 187 | 39 | Calculated (%) | 65.95 | 5.53 | 12.82 |
|  |  |  |  |  |  |  | Found (%) | 65.74 | 5.45 | 12.60 |

TABLE I-continued

Structure: furo-pyrimidine core with substituents R (at position 2 on pyrimidine), Z (at position 4), and CH₃ on furan ring.

| Code No. | R | −Z | Empirical Formula | Molecular Wt. | Melting Point (°C) | Yield % | Elementary Analysis | C | H | N |
|---|---|---|---|---|---|---|---|---|---|---|
| 72 545 | '' | −N(morpholine) | $C_{17}H_{16}ClN_3O_2$ | 329.78 | 226 | 29 | Calculated (%) | 61.91 | 4.89 | 12.74 |
| | | | | | | | Found (%) | 62.01 | 4.87 | 12.56 |
| 72 700 | '' | −N(heptamethyleneimine) | $C_{19}H_{20}ClN_3O$ | 341.83 | 147 | 32 | Calculated (%) | 66.76 | 5.90 | 12.29 |
| | | | | | | | Found (%) | 66.59 | 5.76 | 12.14 |
| 72 682 | '' | −N(octamethyleneimine) | $C_{20}H_{22}ClN_3O$ | 355.86 | 126 | 24 | Calculated (%) | 67.50 | 6.28 | 11.81 |
| | | | | | | | Found (%) | 67.48 | 6.26 | 11.96 |
| 730372 | −CH₃ | −NH−C₆H₄(COOH) | $C_{15}H_{13}N_3O_3$ | 283.28 | 260 | 39 | Calculated (%) | 63.59 | 4.63 | 14.88 |
| | | | | | | | Found (%) | 63.50 | 4.82 | 15.03 |
| 740119 | −CH₃ | −NH−C₆H₄(COOCH₂CH₂−N(morpholine)) | $C_{21}H_{24}N_4O_4$ | 396.43 | 152 | 55 | Calculated (%) | 63.62 | 6.10 | 14.13 |
| | | | | | | | Found (%) | 63.83 | 6.30 | 14.16 |
| 730525 | −CH₃ | −NH−C₆H₄−CO−N(pyrrolidine) + ½ H₂O | $C_{19}H_{20}N_4O_2$ + ½ H₂O | 345.39 | 225 | 20 | Calculated (%) | 66.07 | 6.29 | 16.22 |
| | | | | | | | Found (%) | 66.29 | 6.25 | 16.04 |
| 730508 | −CH₃ | −NH−C₆H₄−CO−N(morpholine) | $C_{19}H_{20}N_4O_3$ | 352.38 | 200 | 44 | Calculated (%) | 63.04 | 6.72 | 15.90 |
| | | | | | | | Found (%) | 64.94 | 5.75 | 15.80 |
| 730693 | −CH₃ | −NH−C₆H₄−OCH₂CH₂−N(morpholine) | $C_{20}H_{24}N_4O_3$ | 368.42 | 134 | 62 | Calculated (%) | 65.20 | 6.57 | 15.21 |
| | | | | | | | Found (%) | 65.15 | 6.78 | 15.25 |

The compounds of formula I have been tested on animals in the laboratory and have been shown to possess antiulcerous, antibronchoconstrictive and anticholinergic, analgesic, antihistaminic, diuretic, cardiovascular analoptic, antiinflammatory and hypertensive properties.

1. ANTIULCEROUS PROPERTIES.

The compounds of formula I, administered by oral means, reduse the extent of gastric ulcers provoked in a rat by typing of the pylorus (Shay ulcers).

Thus, the compound of Code No. 72 498, administered in a dose of 50 mg/Kg/i.d., permits a reduction of 35% of the Shay ulcers in a rat.

2. ANTIBRONCHOCONSTRICTIVE AND ANTICHOLINERGIC PROPERTIES.

Injected by intraduodenal means, the compounds of formula I are capable of opposing the bronchoconstriction provoked in the guinea-pig by the intraveinous injection of acetylcholine and evaluated by the Konzett method.

By way of example, the administration of 100 mg/Kg/i.d. of the compound of Code No. 72 544, permits an inhibition of 50% of the bronchoconstriction provoked in the guinea-pig by the intraveinous injection of acetylcholine.

3. ANALGESIC PROPERTIES.

The compounds of formula I, administered to the mouse or rat by oral means, are capable of reducing the number of painful stretchings caused by the intraperitoneal injection of acetic acid or phenylbenzoquinone and they protect the rat against crying or jumping in the Randall and Selitto test.

BY WAY OF EXAMPLE:

- Table II lists the DE50 of different compounds according to the invention, and
- Table III indicates the results obtained by the administration of 100 mg/Kg/po of other compounds of formula I.

Table II

| Nature of test effected | Code No. of compound tested | Animal | DE 50 (mg/Kg/po) |
|---|---|---|---|
| Test with phenylbenzo-quinone | 730 387 | mouse | 80 |
| | | rat | 43 |
| | 730 372 | mouse | 20 |
| | | rat | 52 |
| | 730 367 | mouse | 72 |
| | | rat | 95 |
| Randall & Selitto test | 730 387 | rat | 42 |
| | 730 372 | rat | 40 |

Table III

| Nature of test effected | Code No. of compound tested | number of painful stretchings (%) |
|---|---|---|
| Test with acetic acid | 730 693 | 70 |
| | 72 545 | 70 |
| Test with phenylbenzo-quinone | 730 508 | 60 |

4. ANTIHISTAMINIC PROPERTIES.

The compounds of formula I, introduced in the conserving medium, are capable of opposing the contractural action of histamine on the isolated ileon of the guinea-pig. This activity is evaluated taking promethazine as standard.

Thus, the compound of Code No. 72561 provides an antihistaminic activity equivalent to 1/15th that of promethazine.

5. DIURETIC PROPERTIES.

The compounds of formula I, administered by oral means to the mouse, simultaneously with a volume of 1 ml. of an isotonic solution of sodium chloride per 25g of the corporeal weight of the mouse, are capable of provoking an augmentation of the volume of urine emitted by reference to control animals, the volume being measured for 6 hours following administration.

Thus, the administration of 25 mg/Kg/po of the compounds of Code Nos. 730 508 and 730387 produced an augmentation of the urinary elimination by 70% and 55%, respectively.

6. CARDIOVASCULAR ANALEPTIC PROPERTIES.

These properties are shown by an augmentation of the force of contractions (positive inotrope action) in the isolated heart of the guinea-pig maintained in a conserving medium and under appropriate experimental conditions.

By way of example, the compounds of Code Nos. 730 387 and 730 372 respectively provoke an augmentation of 75% and of 50% in the force of contractions in a concentration of 0.5 $\mu$g/ml.

7. ANTIINFLAMMATORY PROPERTIES.

The compounds of formula I administered to the rat by oral means, provoke a diminution of the local oedema caused by the sub-plantar injection of carraghenine or Kaolin and oppose the inflammation caused by the Freund adjuvant. Administered by oral means to the guinea-pig, they reduce the erythema caused by ultra-violet irradiation.

The results are listed in the following table IV

| | Percentage diminution of | | | Protection against arthritis by Freund adjuvant | |
|---|---|---|---|---|---|
| Code No. of compound tested | Reduction of oedema with carraghenine or Kaolin DE 50 (mg/Kg/po) | Protection against erythema by ultra-violet | | | |
| | | Dose administered (mg/Kg/po) | Protection (%) | Dose administered (mg/Kg/po) | Protection (%) |
| 730 387 | 38 (carraghenine) | 100 | 60 | — | — |
| 730 372 | 27 (carraghenine) | | | 200 | 55 |
| 730 367 | 6 (Kaolin) 47 (carraghenine) | — 100 | — 50 | — | — |

Also, the administration of the compound of Code No. 730 367 in a dose of 100 mg/Kg/po permits a diminution by 75% of the local oedema caused by the injection of Kaolin.

8. HYPERTENSIVE PROPERTIES.

Administered by intraveinous means, the compounds of formula I provoke an increase in the arterial pressure of an anaesthetised rat.

By way of example, the administration of the compound of Code No. 730 693 in a dose of 2 mg/Kg/i.v., provokes an increase in the arterial pressure of an anaesthetised rat by 25% for a period of the order of 30 minutes.

As a result of a comparison between the pharmacologically active doses mentioned above and the lethal doses listed in the following Table V, the difference between said doses is sufficiently great to permit the utilisation of the compounds of formula I in therapeutics.

| Code No. of compound tested | Dose administered (mg/Kg/po) | Percentage mortality % |
|---|---|---|
| 72 498 | 2000 | 0 |

-continued

| Code No. of compound tested | Dose administered (mg/Kg/po) | Percentage mortality % |
|---|---|---|
| 72 544 | 2000 | 0 |
| 72 561 | 2000 | 0 |
| 72 545 | 2000 | 0 |
| 730 387 | 2000 | 0 |
| 730 372 | 1500 | ≃ 50 |
| 730 367 | 2000 | 0 |
| 730 508 | 2000 | 0 |
| 730 693 | 2000 | ≃ 50 |

The compounds of formula I are useful in the treatment of gastro-duodenal ulcers, visceral spasms, asthma, diverse originating pains and painful inflammations, allergies, oedemas and hypotension.

They may be administered by oral means in the form of tablets, dragees and gelules, containing 50 to 500 mg. of active ingredient (1 to 6 times a day), by parenteral means in the form of injectable ampoules containing 10 to 250 mg of active ingredient (1 to 3 times a day) by rectal means in the form of suppositories containing 25 to 400 mg of active ingredient (1 to 3 times a day) and in the form of suspensions containing 0.5 to 5% of active ingredient (20 to 60 drops, 1 to 3 times a day).

Accordingly, the present invention also relates to a therapeutic composition comprising a compound of the general formula I, together with a therapeutically acceptable carrier.

What we claim is:
1. A compound having the formula

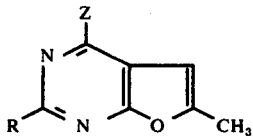

in which R is alkyl having one to 4 carbon atoms, phenyl, or phenyl substituted by at least one halogen or by a trifluoromethyl, Z is 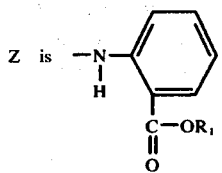

in which $R_1$ is hydrogen or alkyl containing one to 4 carbon atoms.

2. A compound as claimed in claim 1, in which R is methyl and $R_1$ is hydrogen.
3. A compound as claimed in claim 1 in which R is methyl and $R_1$ is methyl.
4. A compound having the formula

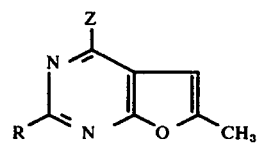

in which R is alkyl having one to 4 carbon atoms, phenyl, or phenyl substituted by at least one halogen or trifluoromethyl, Z is 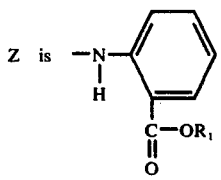

in which $R_1$ is 2,3-dihydroxyprop-1-yl.

* * * * *